Figure 6:
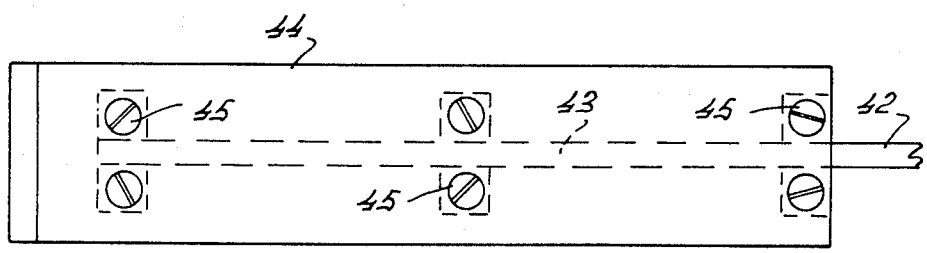

United States Patent [19]

van der Lely

[11] 4,285,284
[45] Aug. 25, 1981

[54] SEEDER WITH PIVOTING SOIL BREAKERS

[76] Inventor: Cornelis van der Lely, Brüschenrain 7, Zug, Switzerland

[21] Appl. No.: 833,286

[22] Filed: Sep. 14, 1977

[30] Foreign Application Priority Data

Sep. 17, 1976 [NL] Netherlands ............... 7610345

[51] Int. Cl.³ ............... A01C 5/06; A01B 11/00
[52] U.S. Cl. ............... 111/85; 172/40; 172/47; 172/60
[58] Field of Search ............... 172/40, 60, 47, 421, 172/439; 37/DIG. 18; 111/1, 85; 267/135

[56] References Cited

U.S. PATENT DOCUMENTS

| 3,170,421 | 2/1965 | Norris et al. | 111/1 |
| 3,296,985 | 1/1967 | Shelton | 172/40 X |
| 3,340,934 | 9/1967 | Wycoff | 111/85 X |
| 3,394,764 | 7/1968 | Higley | 172/40 |
| 3,425,496 | 2/1969 | Shelton | 172/40 |
| 3,514,960 | 6/1970 | Howard | 172/40 X |
| 3,559,744 | 2/1971 | Olinger | 172/47 |
| 3,770,322 | 11/1973 | Cobb et al. | 172/40 X |
| 4,006,832 | 2/1977 | Auxer et al. | 267/135 X |

FOREIGN PATENT DOCUMENTS

| 868666 | 4/1971 | Canada | 172/40 |
| 1154964 | 9/1963 | Fed. Rep. of Germany | 111/1 |
| 1944657 | 3/1971 | Fed. Rep. of Germany | 172/40 |
| 1944658 | 3/1971 | Fed. Rep. of Germany | 172/40 |
| 767411 | 7/1934 | France | 172/40 |
| 781646 | 8/1957 | United Kingdom | 172/47 |
| 1399693 | 7/1975 | United Kingdom | 172/421 |
| 494136 | 3/1976 | U.S.S.R. | 111/1 |

Primary Examiner—Steven A. Bratlie
Attorney, Agent, or Firm—Mason, Mason and Albright

[57] ABSTRACT

A soil cultivating implement has a row of pivotable soil working members linked to a transverse beam of the frame and individual eccentrics are connected to the members to raise and lower soil engaging portions thereof. The portions are pivoted so that the rear parts thereof move through greater amplitudes than front parts of the portions. The frame can be supported by ground wheels which in transport position elevate the soil working members above the ground and this can be accomplished with hydraulic assemblies. The front of the frame can have a resilient coupling to a prime mover to reduce shocks induced by the eccentric drives. Dispensing mechanisms can be positioned to the rear of the soil working members to dispense and/or seed the worked ground.

22 Claims, 14 Drawing Figures

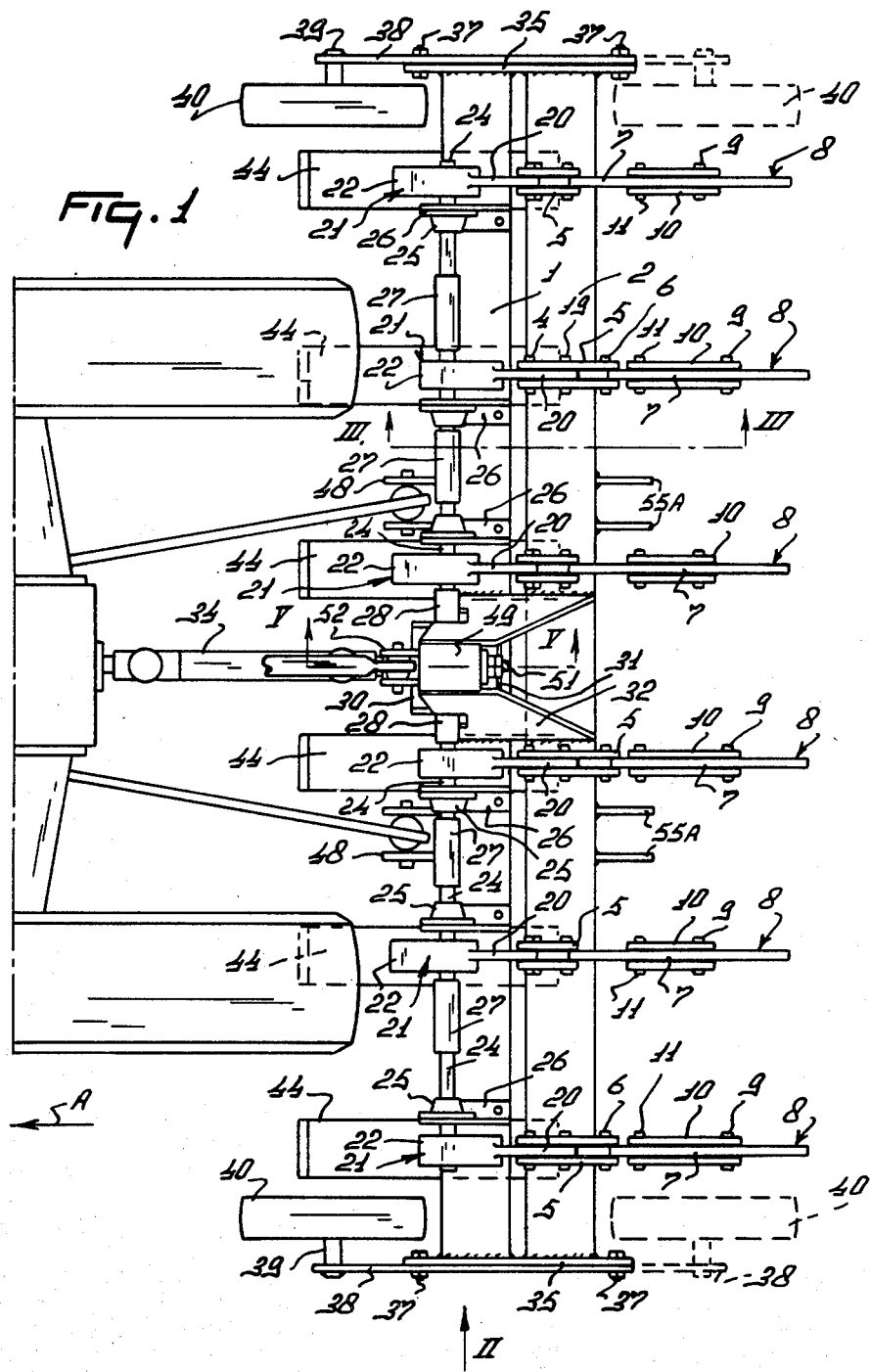

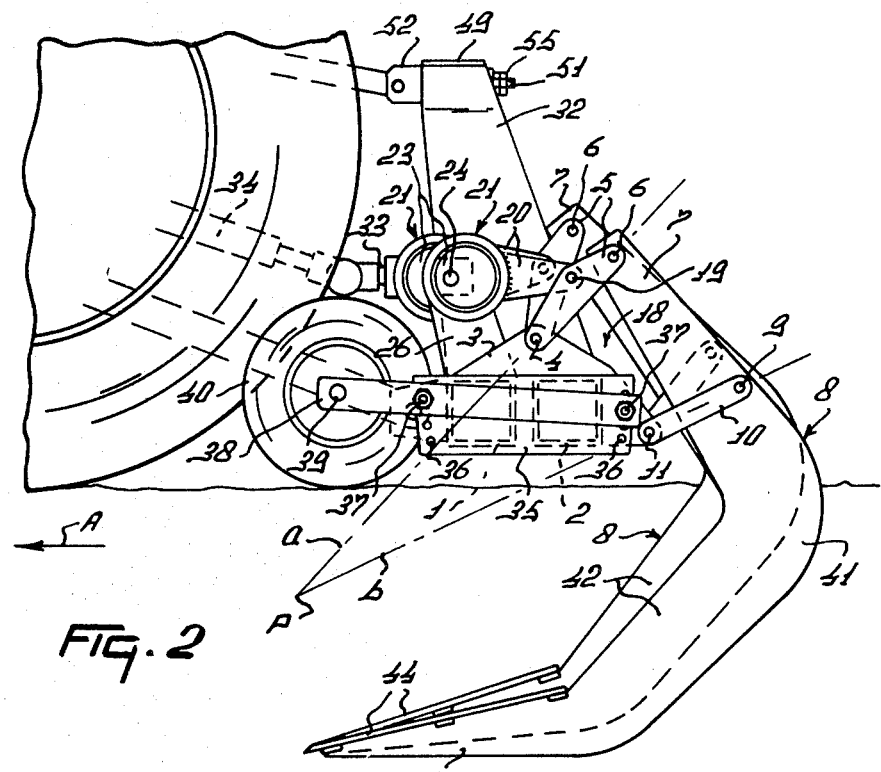
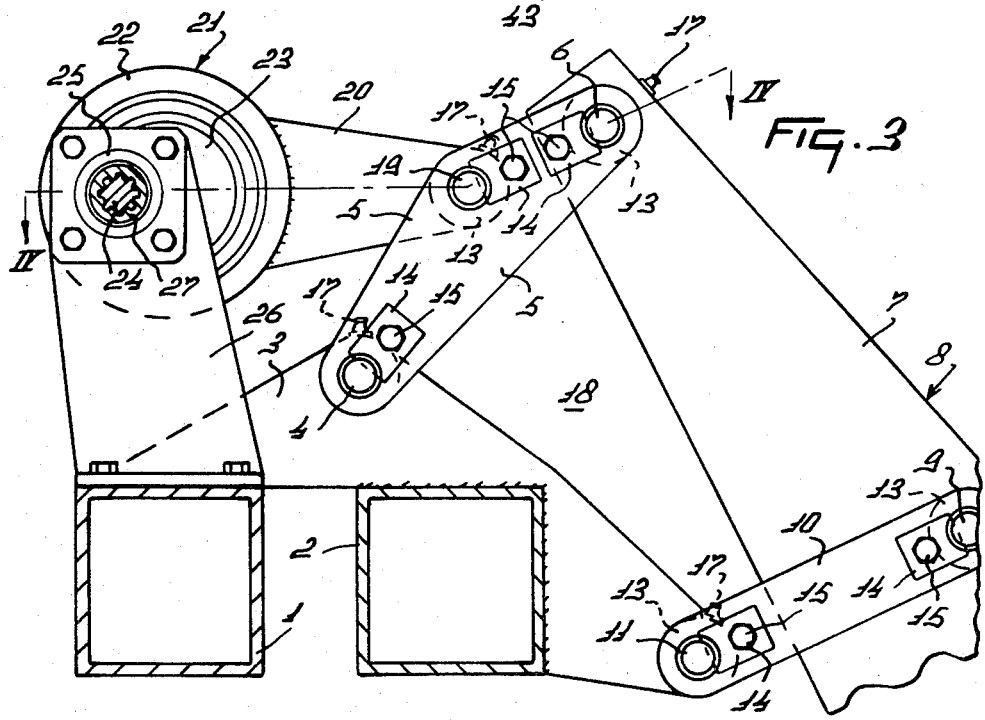

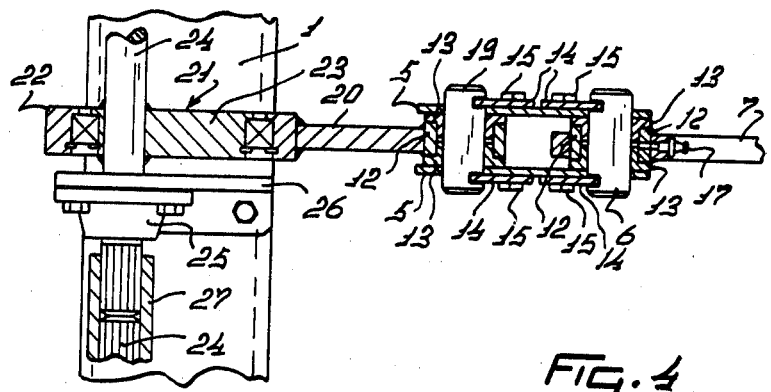
FIG. 4
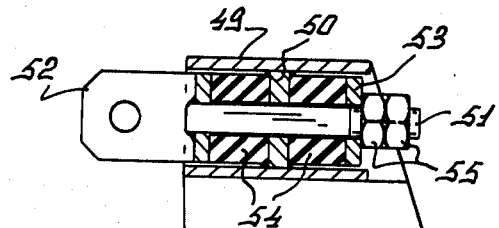
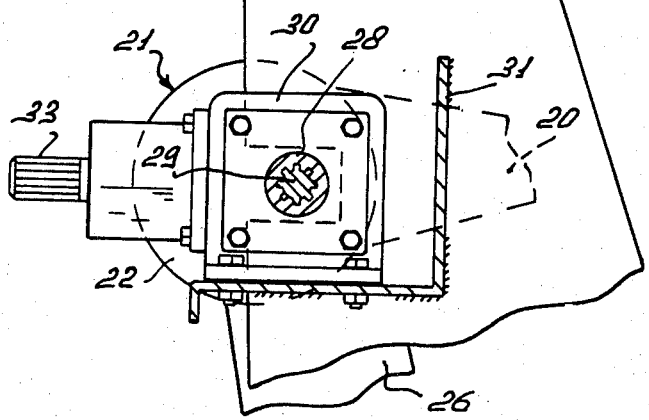
FIG. 5

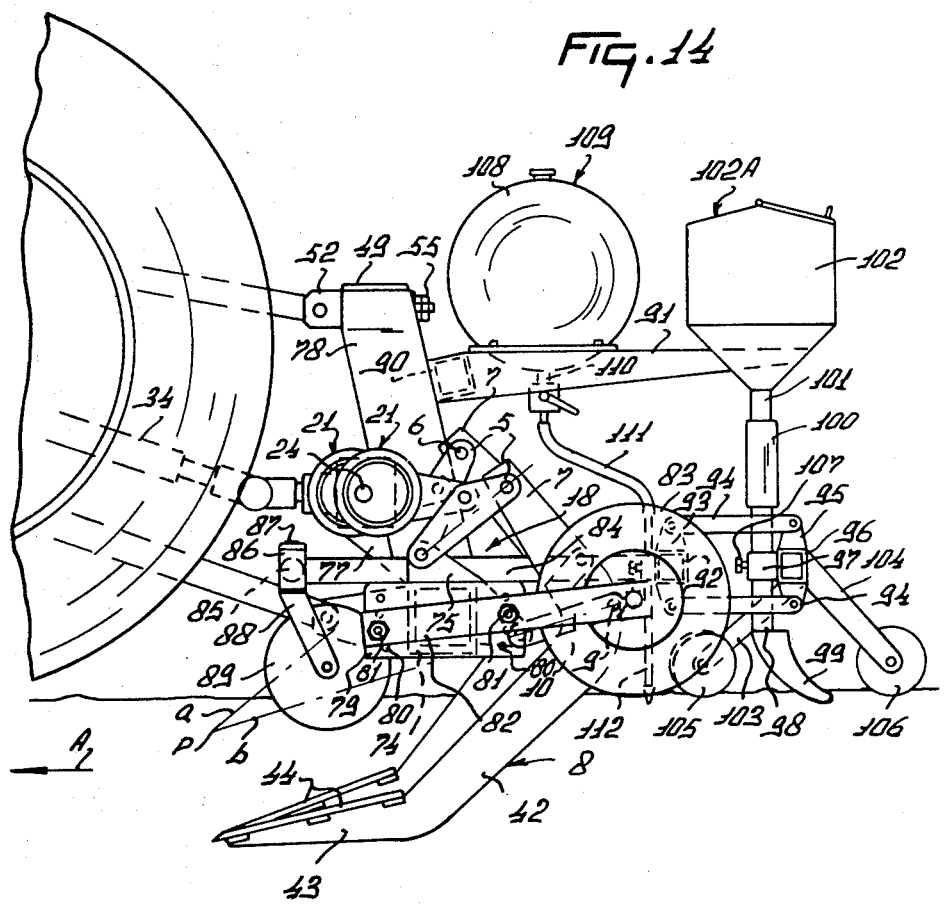

SEEDER WITH PIVOTING SOIL BREAKERS

According to one aspect of the invention, there is provided a soil cultivating implement of the kind set forth, wherein each of at least a number of said soil working members is separately connected to the frame by an individual pivotable polygonal linkage whose construction and disposition above the ground surface is such that, during operation, the rear of the corresponding soil working member with respect to the direction of operative travel of the implement will perform a repetitive movement of greater amplitude than that performed by the front of said member.

Figure 7:
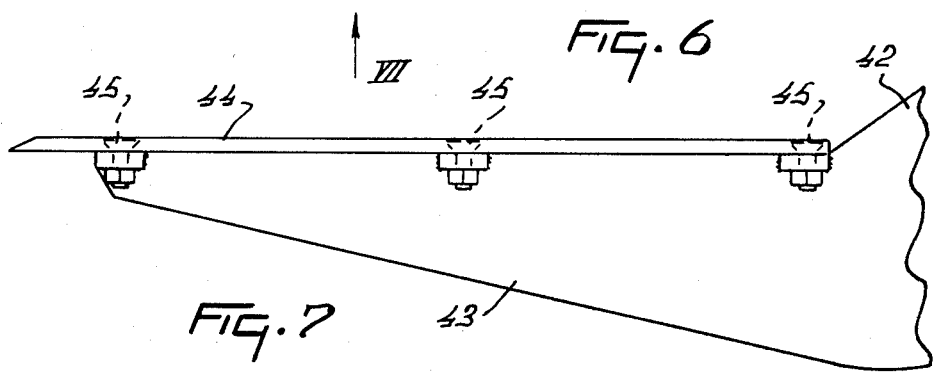
Figure 8:
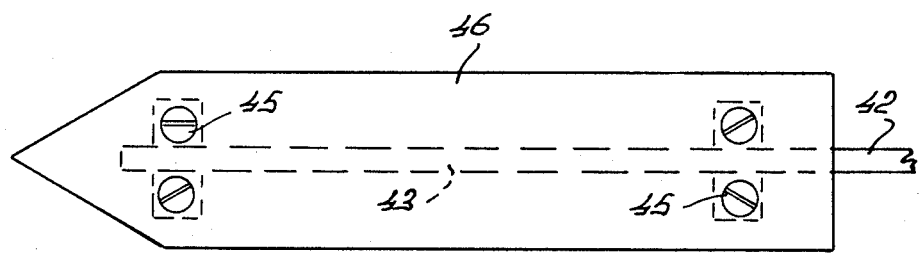
Figure 9:
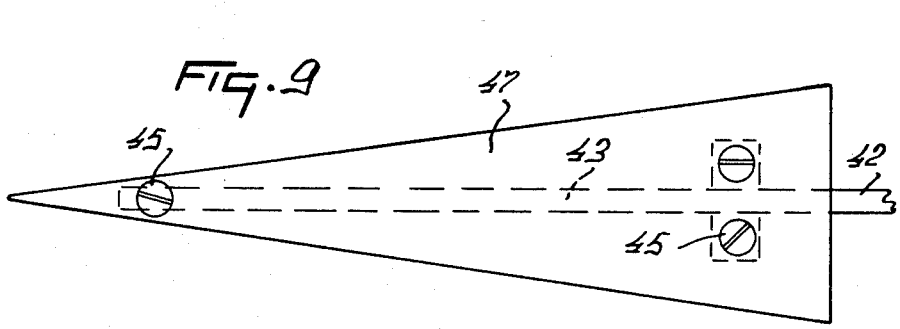
Figure 10:
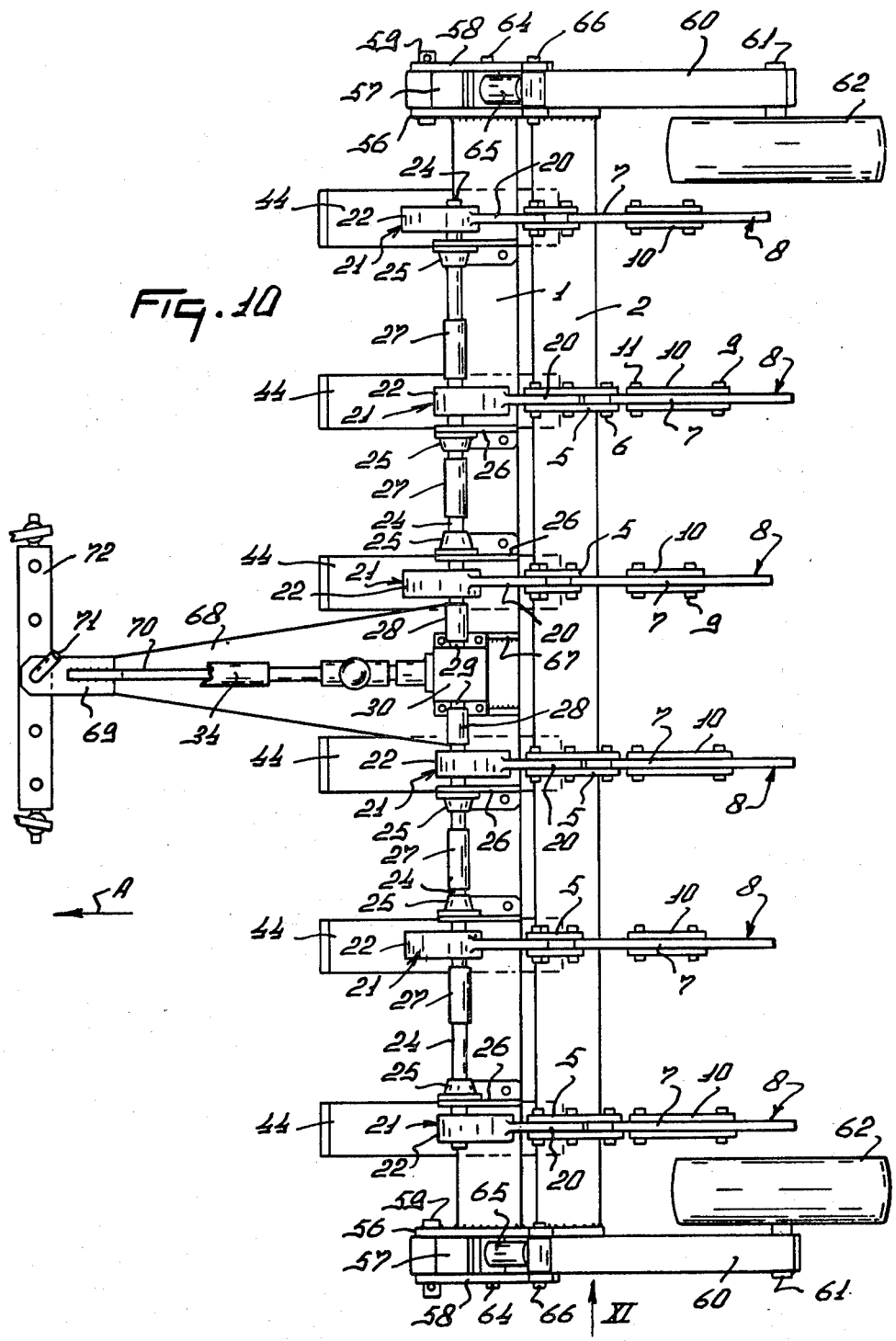
Figure 11:
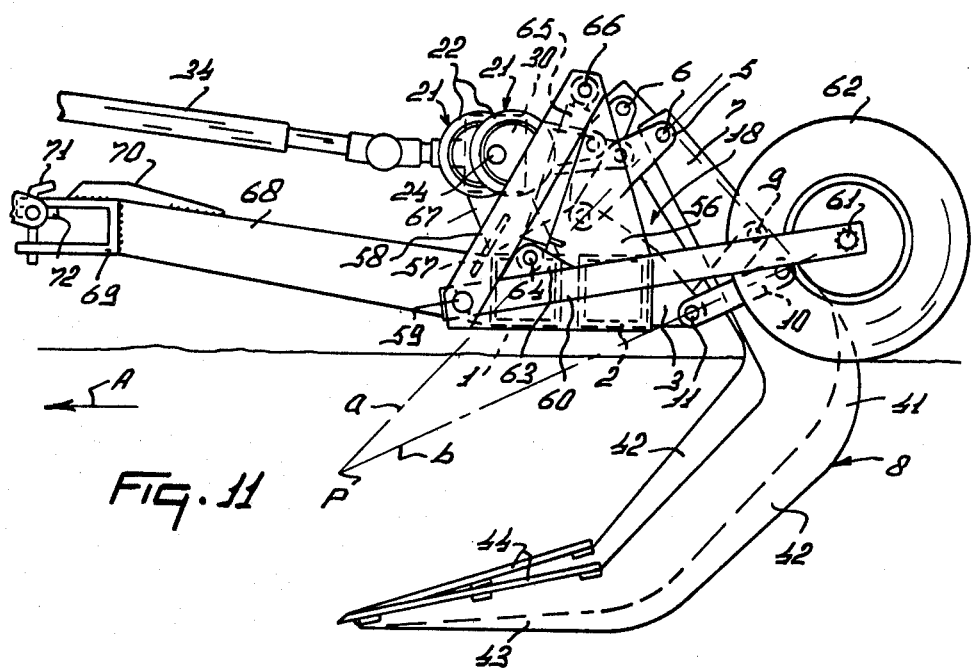
Figure 12:
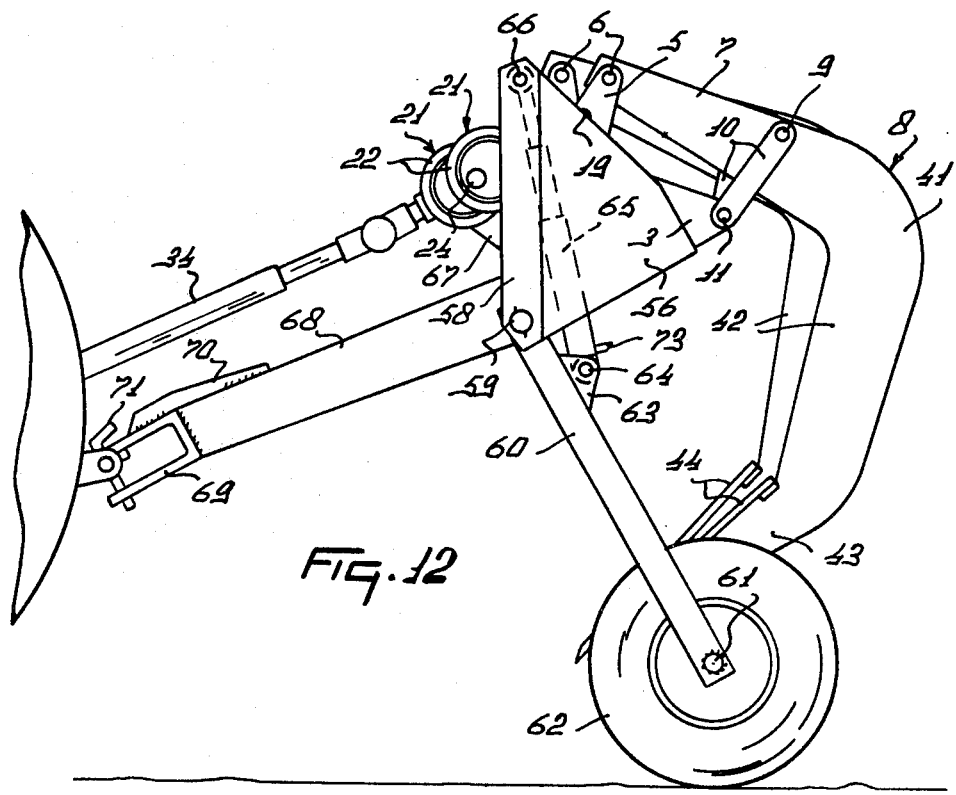
Figure 13:
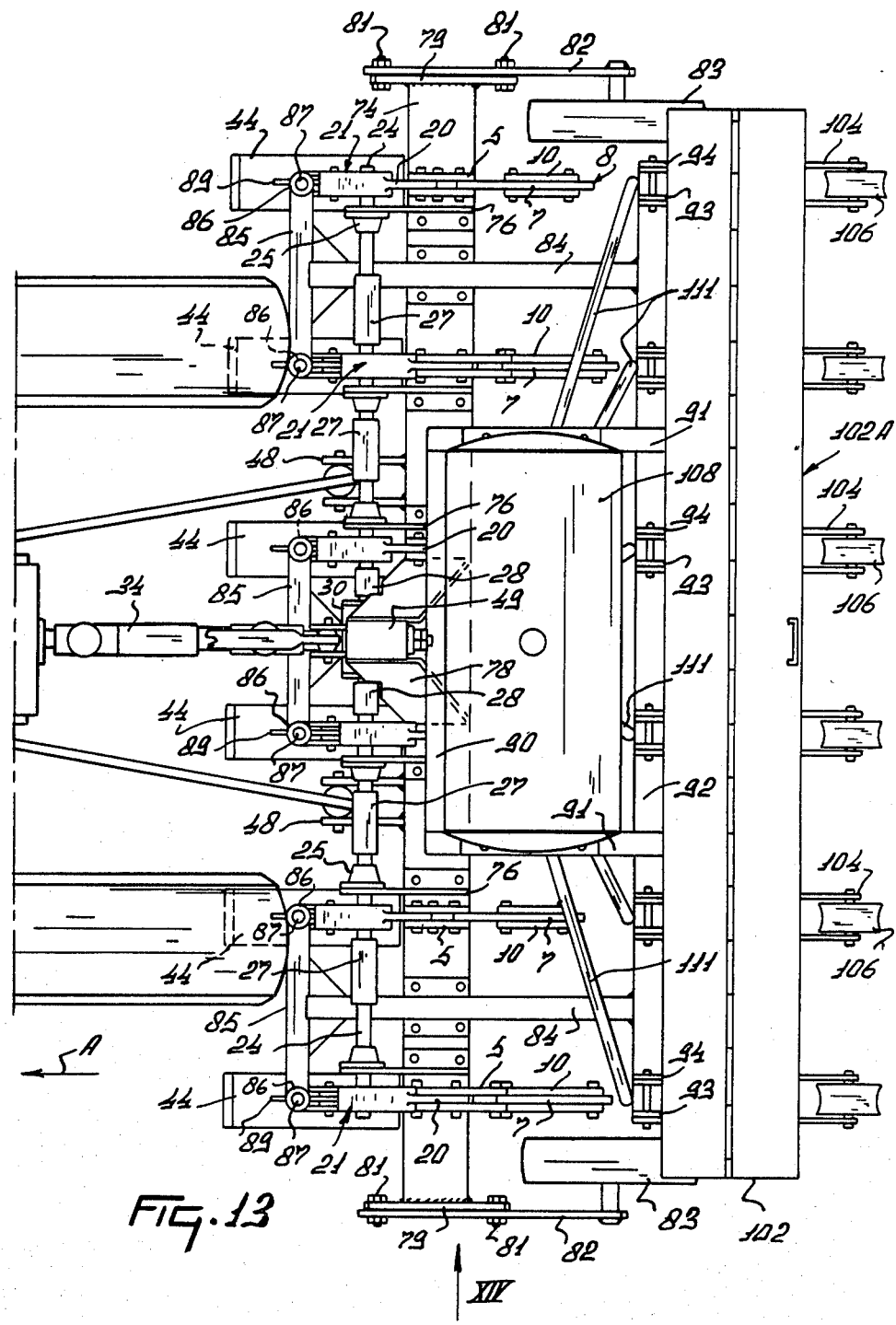

For a better understanding of the invention, and to show how the same may be carried into effect, reference will now be made, by way of example, to the accompanying drawings, in which:

FIG. 1 is a plan view of a soil cultivating implement in accordance with the invention connected to the rear of an agricultural tractor, FIG. 2 is a side elevation, to an enlarged scale, as seen in the direction indicated by an arrow II in FIG. 1, FIG. 3 is a section, to an enlarged scale, taken on the line III—III in FIG. 1, FIG. 4 is a section taken on the line IV—IV in FIG. 3, FIG. 5 is a section, to an enlarged scale, taken on the line V—V in FIG. 1, FIG. 6 is an elevation of one of the parts of the implement of FIGS. 1 to 5 to an enlarged scale and in greater detail, FIG. 7 is a view as seen in the direction indicated by an arrow VII in FIG. 6, FIG. 8 is a similar view to FIG. 6 but illustrates an alternative embodiment of said part, FIG. 9 is a view similar to FIGS. 6 and 8 and illustrates a further alternative embodiment, FIG. 10 is a plan view of an alternative form of soil cultivating implement in accordance with the invention connected to the rear of an operating vehicle, FIG. 11 is a view as seen in the direction indicated by an arrow XI in FIG. 10, FIG. 12 corresponds to FIG. 11 but illustrates the arrangement of the implement in an inoperative transport position, FIG. 13 is a plan view of a third form of soil cultivating implement in accordance with the invention connected to the rear of an agricultural tractor, and FIG. 14 is a side elevation as seen in the direction indicated by an arrow XIV in FIG. 13.

Referring to FIGS. 1 to 7 of the accompanying drawings, the soil cultivating implement or machine that is illustrated therein has a frame which comprises two beams 1 and 2 that are parallel to one another and both of which extend substantially horizontally transverse, and usually substantially horizontally perpendicular, to the intended direction of operative travel of the implement that is indicated throughout the drawings by an arrow A, the two beams 1 and 2 being located at the same, or substantially the same, horizontal level with the beam 1 spaced a short distance forwardly from the beam 2 with respect to the direction A. The two beams 1 and 2 are both of hollow formation and both of them have a polygonal cross-section which is preferably, but not essentially, the square cross-section that is illustrated in the drawings since this readily allows the lower surfaces of the beams to be horizontally or substantially horizontally disposed. The upper surfaces of the two beams 1 and 2 are rigidly interconnected by six support plates 3 which are substantially vertically parallel to one another and parallel or substantially parallel to the direction A, said support plates 3 being spaced apart from one another by regular distances which advantageously have magnitudes of between substantially 60 centimeters and substantially 75 centimeters, the end plates 3 of the row of six plates also being spaced from the opposite ends of the beams 1 and 2 by distances which are substantially half the size of the spacing between the plates 3 themselves that has just been mentioned. As seen in side elevation (FIGS. 2 and 3), that part of each support plate 3 which is disposed above the frame beams 1 and 2 is of substantially isosceles triangular configuration, the base thereof being fastened to the tops of the beams 1 and 2.

Pairs of arms 5 of round-cornered triangular configuration are turnably connected to opposite sides of the apex of each support plate 3 by horizontal stub shafts 4 that extend parallel to the frame beams 1 and 2, said pairs of arms 5 being inclined obliquely upwardly and rearwardly, with respect to the direction A, away from the corresponding stub shafts 4 (see FIG. 3). Further stub shafts 6 that are parallel to the stub shafts 4 pivotally connect the upper rear ends of the pairs of arms 5 to the opposite sides of the upper ends of fastening portions 7 of corresponding soil working members in the form of rigid hook-shaped tines 8 that will be further described below. Towards the lower end of each tine fastening portion 7, a stub shaft 9 which projects from opposite sides of that portion in parallel relationship with the stub shafts 4 and 6 connects the upper rear ends of two links 10 to said portion 7 so that said links 10 lie at opposite lateral sides thereof and extend downwardly and forwardly from said stub shaft 9 with respect to the direction A. The links 10 project beyond the leading edge of each tine fastening portion 7 and their lower leading ends are pivotally connected by a further substantially horizontal stub shaft 11 to the opposite sides of a downward and rearward extension of a corresponding one of the six support plates 3 (see FIG. 3).

FIGS. 3 and 4 of the drawings illustrate the relative dispositions of each group of stub shafts 4, 6, 9 and 11 and the disposition of the pair of arms 5 and pair of links 10 that interconnect those stub shafts. FIG. 4 shows that the illustrated tine fastening portion 7 is formed with a transverse hole in which a cylindrical bush 12 is secured by welding. The bush 12 receives, from its opposite ends, two cylindrical sleeves 13 that have outwardly directed flanges at their outer ends. The outer diameters of the sleeve flanges are the same as the external diameter of the bush 12 and, when said sleeves 13 are entered into their correct positions in the bush 12, their inner axial ends are nearly, but not quite, in contact with one another midway along the length of the bush 12. The two sleeves 13 co-operate to form a pivot bearing around the stub shaft 6. The stub shaft 6 is maintained in its appointed position by having the ends of two blocking plates 14 entered into slots that are formed in its curved surface near its opposite ends. The two blocking plates 14 are secured to the two arms 5 of the corresponding pair by bolts 15. This arrangement that has been described for one of the stub shafts 6 is repeated for the three stub shafts 4, 9 and 11 of the corresponding group and for all four of the stub shafts 4, 6 9 and 11 of the other five groups. Lubrication for each pivot bearing is afforded by forming the bushes 12 with radial bores that communicate with bores in mountings for grease nipples 17, said mountings being secured to the external surfaces of the bushes 12. The internal ends of the bores in the bushes 12 communicate with the small spaces between the axially opposed inner ends of the two sleeves 13 of each pivot bearing. It will be seen from the drawings that the grease nipples 17 for the pivot bearings that comprise the stub shafts 4 and 11 are located substantially vertically above those stub shafts whereas the grease nipples 17 for the pivot bearings that comprise the stub shafts 6 and 9 are located above and to the rear of those stub shafts 6 and 9 with respect to the direction A.

Each tine 8 is pivotable upwardly and downwardly relative to the frame of the implement by way of a pivotable quadrilateral linkage 18 that comprises the corresponding arms 5, links 10 and pivot bearings that include the stub shafts 4, 6, 9 and 11. These four stub shafts are, as seen in FIG. 2 of the drawings, at the four corners of a quadrilateral which is not, however, a parallelogram, a line a which intersects the longitudinal axes of the two stub shafts 4 and 6 that can be seen in FIG. 2 of the drawings meeting a line b which intersect the longitudinal axes of the two stub shafts 9 and 11 that can be seen in the same Figure of the drawings at a point P which, it will be noted is substantially vertically above the leading lowermost extremity of the corresponding tine 8 at a location which is below the ground surface when the implement is in use. The position of the point P is determined by the particular shape of the polygonal linkage 18 and the fact that the distance between the stub shafts 4 and 11 thereof is less than the distance between the stub shafts 6 and 9 thereof, the former distance preferably not being less than substantially four-fifths of the latter distance. It will be noted that the line a in FIG. 2 is substantially parallel to the length of each arm 5 which, despite being of shallow triangular configuration, actually departs only marginally from a rectilinear configuration. Similarly, the line b is parallel to the longitudinal axis of each link 10 as seen in FIG. 2 of the drawings.

The shallow "apex" corners of each pair of arms 5 are connected by a pivot bearing which comprises a stub shaft 19 to the rear end of a corresponding arm 20, the pivot bearings which include the six stub shafts 19 all being of the same construction as has been described above in detail for the pivot bearing that comprises one of the stub shaft 6. Each arm 20 projects forwardly with respect to the direction A from between the corresponding pair of arms 5 and its leading end is welded to the outer surface of a ring 22 that forms part of a corresponding eccentric mechanism which is generally indicated by the reference 21. The ring 22 rotatably surrounds, with the aid of an intervening bearing, a disc 23 that is rigidly secured to a shaft 24 with its center spaced from the longitudinal axis of that shaft, the disc 23 thus being eccentric with respect to the shaft 24. The shaft 24 is a rotary shaft which extends substantially horizontally perpendicular to the direction A in parallel relationship with the frame beams 1 and 2. There are, in fact, a plurality of the shafts 24, one for each eccentric mechanism 21, arranged in axially aligned relationship, each individual shaft 24 being rotatably journalled in horizontal bearings 25 whose housings are secured to brackets 26 which project upwardly, and forwardly with respect to the direction A at a few degrees to the vertical, from the top of the leading frame bram 1 (see FIGS. 3 and 4 of the drawings). The adjoining or at least adjacent ends of the axially aligned shafts 24 are splined and are releasably interconnected by surrounding internally splined sleeves 27 (FIG. 4) except for the two shafts 24 that project towards one another substantially midway across the width of the implement, the splined ends of these two shafts 24 being connected by internally splined sleeves 28, that are similar to the sleeves 27, to the opposite splined ends of a horizontally disposed output shaft 29 of a central gear box 30 of the implement (see FIG. 5). The shaft 29 is provided, inside the gear box 30, with a bevel pinion (not visible) whose teeth are in driven mesh with those of a further bevel pinion (also not visible) carried by a rotary input shaft 33 of said gear box, the leading splined end of said input shaft 33 projecting forwardly from the front of the gear box in substantially the direction A. The central gear box 30 is bolted to a support 31 which rigidly interconnects the upwardly convergent limbs of a central coupling member or trestle 32 of the implement. The lower ends of said limbs of the coupling member or trestle 32 are rigidly welded to the upper surfaces of the frame beams 1 and 2. The forwardly projecting splined end of the rotary input shaft 33 of the central gear box 30 of the implement is intended to be placed in driven connection with the rear power take off shaft of an agricultural tractor or other operating vehicle through the intermediary of a telescopic transmission shaft 34 (FIG. 1) that is of a construction which is known per se having universal joints at its opposite ends.

The ends of the frame beams 1 and 2 of the implement frame are rigidly interconnected by substantially vertical side plates 35 of said frame which side plates are parallel to each other and parallel or substantially parallel to the direction A, said side plates 35 both being extended forwardly of the main frame beam 1 and rearwardly of the rear frame beam 2 with respect to the direction A (see FIG. 2) to terminate in leading and rear edges that are in upwardly divergent relationship by a few degrees. The portions of the two side plates 35 of the implement frame that project in front of, and behind, the frame beams 1 and 2 are formed with curved rows of holes 36 through chosen ones of which corresponding bolts 37 can be horizontally entered to secure arms 38 in chosen positions along-side the plates 35, each arm 38 being formed with only two holes one of which can register with any chosen one of the rear row of holes 36 in the adjoining side plate 35 and the other one of which can register with any chosen one of the holes 36 in the leading row thereof in the same plate 35. The two arms 38 project forwardly beyond the leading upwardly and forwardly inclined edges of the corresponding frame side plates 35 and, at its leading end, each arm 38 carries a corresponding substantially horizontally disposed axle shaft 39 at the side of that arm 38 which faces inwardly towards the center of the implement. Each axle shaft 39 has a corresponding pneumatically tired ground wheel 40 mounted thereon in a freely rotatable manner. It will be appreciated that the level of the frame of the implement above the ground which is maintained during operative progress of the implement in the direction A is set by placing the axle shafts 39 of the ground wheels 40 at a chosen level relative to said frame. This is achieved by connecting each arm 38 to the corresponding frame side plate 35 at a chosen level by entering the corresponding bolt 37 through an appropriate one of the rear row of holes 36 and then turning said arm 38 upwardly or downwardly about the axis of the rear bolt 37, before finally tightening the latter, until the respective leading bolt 37 can be entered through an appropriate hole 36 in the leading row thereof in the same side plate 35. The bolts 37 are firmly tightened once the required level of the frame above the ground surface has been attained for a particular cultivating operation. In addition to the upward and downward adjustability of the ground wheels 40 relative to the frame of the implement in the manner that has just been described, each arm 38 can be disconnected from the corresponding frame side plate 35 and can be reconnected thereto in such a position that its associated ground wheel 40 is located to the rear of the frame beam 1 and 2 with respect to the direction A instead of in front thereof. One such position of the two ground wheels 40 is shown in broken lines in FIG. 1 of the drawings and it will be realised that bodily upward and downward adjustment thereof relative to the frame of the implement remains equally possible since the two holes in each arm 38 will still co-operate with chosen holes 36 in the corresponding frame side plate 35 by way of the two bolts 37.

Each tine 8 is principally of flat strip-shaped or planar construction and, in addition to its upper downwardly and rearwardly inclined fastening portion 7 that increases in width (in the direction A) from top to bottom (see FIGS. 2 and 3), it comprises a forwardly and downwardly inclined substantially straight portion 42 that is integrally connected to its lower end by a corresponding bend 41, said portion 42 being of decreasing width (in the direction A) from top to bottom. The downwardly and forwardly inclined lower portion 42 of each tine 8 terminates integrally in a forwardly directed portion 43 whose lowermost edge is substantially horizontally parallel to the direction A when the tine 8 concerned is at substantially the lowest position which it can attain by movement of the corresponding pivotable quadrilateral linkage 18 (see FIG. 2). However, the portions 43 taper forwardly in the direction A and their upper edges are thus inclined downwardly and forwardly with respect to the direction A to meet the locally deformed lower edges at blunt tips (FIG. 7). The upper edge of each portion 43 defines a supporting surface for a corresponding element in the form of a flat blade 44, said blade 44 being of an oblong shape (see FIG. 6) Which is elongate in the same direction as the upper edge of the portion 43 concerned, the leading narrow edge of the blade being bevelled to form a chisel edge (see FIGS. 6 and 7). The upper edge of each portion 43 is provided at three locations at its opposite sides with apertured lugs and six countersunk holes in each blade 44 will register with the apertures in any group of these lugs so that the blades 44 can be firmly but releasably secured to said lugs by six short bolts 45 that have countersunk heads for co-operation with the countersunk holes in the blade 44 concerned. It will be seen from FIGS. 2, 6 and 7 of the drawings that each blade 44 extends throughout the whole length of the upper edge of the corresponding forwardly directed tine portion 43 and actually projects forwardly beyond the leading end of that edge by some distance.

FIG. 8 of the drawings illustrates an alternative element in the form of a blade 46 that is elongate in the same direction as the blade 44. However, the leading end of the blade 46 comes to a sharp V-shaped point and is secured by four of the bolts 45 to four, rather than six, of the lugs that project from opposite sides of the upper edge of the corresponding tine portion 43. FIG. 9 illustrates a further alternative blade 47 that is of isosceles triangular configuration, the narrow base of the triangle being rearmost with respect to the direction A and the sharp apex thereof being foremost. In this case, three of the bolts 45 are employed to secure the blade 47 firmly but releasably to two lugs, the third and leading bolt 45 having its shank entered through a bore formed in the material of the corresponding tine portion 43 close to the leading end or tip of that portion.

In addition to the upwardly convergent portions of the coupling member or trestle 32 that have been described above, said coupling member or trestle comprises two pairs of lugs 48 which project forwardly with respect to the direction A from the frame beam 1 at equal distances from the midpoint of that frame beam. The lugs 48 of each pair are apertured to receive pivots that extend substantially horizontally parallel to the frame beams 1 and 2 and said pivots are employed in the manner that is illustrated somewhat diagrammatically in FIG. 1 of the drawings in releasably connecting the free rearmost ends of the lower lifting links of a three-point lifting device or hitch of an agricultural tractor or other operating vehicle to said lugs. The uppermost ends of the upwardly convergent plates at the center of the coupling member or trestle 32 are interconnected by a housing 49 (FIGS. 1 and 5) that has a polygonal cross-section which is preferably, as illustrated, square. The interior of the housing 49 is provided, substantially midway between its opposite ends, with a transverse plate 50 through a central hole in which extends a rod 51 that is parallel or substantially parallel to the direction A. The leading end of the rod 51 is welded to the base of a fork 52 whose limbs project forwardly from the front of the housing 49 with respect to the direction A, said limbs being formed with substantially horizontally aligned holes for co-operation with a pivot at the rearmost end of the upper adjustable length lifting link of the three-point lifting device or hitch of the agricultural tractor or other operating vehicle to which the implement is connected in the use thereof. Two resilient apertured blocks 54 that may be formed from natural rubber, synthetic rubber or a synthetic plastics material having resilient properties are arranged with their apertures around the rod 51 between the base of the fork 52 and the plate 50 and between the plate 50 and a washer 53, respectively, the washer 53 being mounted on the rod 51 towards the rearmost and thereof but just inside the rear end of the housing 49, its peripheral shape matching the cross-section shape of the housing 49 itself. The rearmost end of the rod 51 is screwthreaded and bears an axially displaceable nut 55 and a co-operating lock nut that is also indicated by the reference 55. It will be apparent from FIG. 5 of the drawings that the leading nut 55 with respect to the direction A bears against the rear surface of the washer 53 which latter thus affords a stop.

In the use of the soil cultivating implement that has been described with reference to FIGS. 1 to 7 of the drawings, its coupling member or trestle 32 is connected to the three-point lifting device or hitch at the rear of an agricultural tractor or other operating vehicle employing the fork 52 and the lugs 48 in the manner that has been described above. The rotary input shaft 33 of the central gear box 30 is placed in driven connection with the rear power take-off shaft of the same tractor or other vehicle by way of the known telescopic transmission shaft 34 that has universal joints at its opposite ends. The working depth of the tires 8, which agitate the sub-coil during the operation of the implement, can be adjusted, before work commences, by moving the ground wheels 40 bodily upwardly or downwardly relative to the frame of the implement employing the arms 38, the bolts 37 and the holes 36 in the manner that has been described above. The implement is supported from the ground surface in a particularly effective manner if the ground wheels 40 are disposed in front of the frame beams 1 and 2 with respect to the direction A and this position of the ground wheels 40 is desirable when very hard soil is to be dealt with. However, as previously discussed, the ground wheels 40 can, alternatively, be disposed rearwardly of the frame beams 1 and 2 with respect to the direction A as shown in broken lines in FIG. 1 of the drawings. Rotary drive applied to the input shaft 33 of the gear box 30 causes the output shaft 29 thereof and the coaxial composite shaft 24 to revolve about their common longitudinal axis and the implement occupies a working position such as the one which is shown, for example, in FIG. 2 of the drawings. Each of the hook-shaped tines 8 tears up the soil during operative progress in the direction A and is effective to a depth dependent upon the pre-adjusted level of the ground wheel axle shafts 39 relative to the level of the frame of the implement. The blades 44 on the upper edges of the leading forwardly directed portions 43 of the tines 8 act as wedges and their significant but constantly varying inclinations to the horizontal ensure that the sub-soil through which they pass is lifted and well broken up by agitation. It has been found to be advantageous to provide one of the eccentric mechanisms 21 for each of the six tines 8 since said tines 8 then all operate effectively, their agitating action upon the sub-soil being consistently satisfactory throughout the working width of the implement. It will be seen from FIG. 2 of the drawings that the eccentric discs 23 which correspond to two immediately neighbouring mechanisms 21 are offset through substantially 180° relative to one another about the longitudinal axis of the composite shaft 24 as regards their respective eccentricities and this facilitates a balanced action of the implement since the forces that are generated by three tines 8 moving downwardly at any instant are substantially counterbalanced by the forces generated by the other three tines 8 which are moving upwardly at the same instant.

Each eccentric mechanism 21 causes the corresponding tine to perform an upward and downward vibratory motion during operative progress in the direction A, said motion being transmitted by the corresponding arm 20, pair of arms 5 and pair of links 10 to the fastening portion 7 of said tine 8. The previously discussed configuration of the pivotable quadrilateral linkage 18 which includes said arms 5 and links 10 is such that the leading edge of the blade 44 remains at a substantially constant depth below ground level while the amplitude of the repetitive vertical displacement of points along the length of the tine 8 become greater as the distance rearwardly therefrom increases and the distance from the uppermost end of the fastening portion 7 of the tine becomes less. Despite the balancing effect that is produced by the described relative offset of the immediately neighbouring discs 23 along the composite shaft 24, there will inevitably be some vibration, jolting and the like that is attributable to the passage of the tines 8 through the soil but the transmission of this vibration and the like to the agricultural tractor or other vehicle which is towing and operating the implement is minimised, if not completely overcome, by the provision of the rubber or other resilient blocks 54 (FIG. 5) in the housing 49 at the top of the upwardly convergent plates of the coupling member or trestle 32. The effect of the blocks 54 can be adjusted by moving the nuts 55 along the screwthreaded portion of the rod 51 to increase or decrease the initial compression of said blocks 54 between the washer 53 and the base of the fork 52. It is noted that two pairs of lugs 55A (FIG. 1) are provided in horizontally spaced apart relationship at the rear of the frame beam 2 so that an agricultural implement or machine that is to be employed in conjunction with the soil cultivating implement can be connected to said lugs 55A to follow immediately behind the soil cultivating implement in register with the path of travel of the latter. Such additional implement or machine could, for example, be a seed drill, a planting machine and/or an implement or machine for feeding fertiliser and/or other material into and/or onto the ground.

FIGS. 10 to 12 of the drawings illustrate an alternative form of soil cultivating implement or machine in accordance with the invention which implement or machine is similar or identical, in many respects, to the implement or machine that has already been described and, accordingly, parts of the implement of FIGS. 10 to 12 of the drawings, and of the further implement of FIGS. 13 and 14 of the drawings, that are similar or identical to parts which have already been described are indicated by the same references as have been used in FIGS. 1 to 9 of the drawings. In the embodiment of FIGS. 10 to 12 of the drawings, the ends of the frame beams 1 and 2 are rigidly interconnected by substantially, although not exactly, triangular side plates 56 whose leading corners are disposed in advance of the frame beam 1 with respect to the direction A, the apex of each side plate 56 being disposed at a distance above the tops of the frame beams 1 and 2 when the implement or machine occupies the working position thereof that is illustrated in FIGS. 10 and 11. Each side plate 56 has a corresponding strip 58 rigidly connected to it in spaced relationship by an intervening transverse piece 57 which is located near one end of the strip 58 concerned. The general plane of each strip 58 is substantially vertically parallel to that of the corresponding side plate 56 and is thus substantially vertically parallel to the direction A. In a working position of the implement of FIGS. 10 to 12 of the drawings, each strip 58 extends steeply upwardly and rearwardly with respect to the direction A (see FIG. 11), its lower leading end being perpendicularly connected to the forwardly projecting portion of the corresponding side plate 56 by a substantially horizontal stub shaft 59. The leading end, with respect to the direction A, of an arm 60 is turnable upwardly and downwardly about each stub shaft 59 between the corresponding side plate 56 and strip 58, the arms 60 extending generally rearwardly from the stub shafts 59 and being provided, at their rearmost ends, with corresponding axle shafts 61 that project inwardly towards the center of the implement from the arms 60 concerned. Each axle shaft 61 has a corresponding pneumatically tired ground wheel 62 rotatably mounted thereon. The top of each arm 60 is provided, at a short distance from the corresponding stub shaft 59, with a pair of upwardly projecting lugs 63 between which a corresponding substantially horizontal pivot pin 64 is mounted. The base end of the cylinder of a corresponding hydraulic piston and cylinder assembly 65 is turnably mounted on each pivot pin 64 between the lugs 63 of the corresponding pair, the free end of the piston rod of the same assembly 65 being connected by a further substantially horizontal pivot pin 66 to the apex of the corresponding substantially triangular side plate 56 and the upper end of the neighbouring strip 58.

In this embodiment, the central gear box 30 is sustained from the leading frame beam 1 by a support 67 that is welded or otherwise rigidly secured to the top of said frame beam 1 midway along the transverse length thereof. Moreover, the front of the leading frame beam 1 with respect to the direction A has one end of a forwardly projecting draw bar 68 rigidly secured to it, said draw bar 68 tapering forwardly away from a central region of the transverse length of the frame beam 1 in the manner that can be seen in FIG. 10 of the drawings. The leading end of the draw bar 68 with respect to the direction A carries a coupling fork 69 whose connection to said draw bar 68 is strengthened by the provision of an upright rib 70. A hitch pin 71 which will be substantially vertically disposed when the implement is in use is provided to connect the fork 69 pivotally to a tow bar 72 or the like at the rear of an agricultural tractor or other towing and operating vehicle. Each of the two hydraulic piston and cylinder assemblies 65 is a single-acting assembly having a duct connection 73 that is coupled by known rigid and flexible hydraulic conduits (not shown) to the hydraulic system of the agricultural tractor or other vehicle that is employed to tow and operate the implement.

When the implement is in use, it occupies substantially the position thereof that is illustrated in FIGS. 10 and 11 of the drawings in which position the tines 8 break up the soil with a lifting action and have a strong agitating effect upon the subsoil. Once again, either the blades 46 or 47 can be used in place of the blades 44 having regard to the nature and condition of the soil that is to be dealt with. In this embodiment, the depth at which the tines 8 will penetrate into the soil during operation is controlled by moving the ground wheels 62 bodily upwardly and downwardly relative to the implement frame by changing the angular positions of the arms 60 about the pivot pins 59. This is achieved by operation of the hydraulic system of the towing tractor or other vehicle and it will be apparent from FIGS. 11 and 12 of the drawings that the greater the volume of oil or other hydraulic pressure medium that is supplied to the assembly 65, the higher the frame will be lifted above the ground surface and the smaller will be the depth of penetration of the tines 8 into the soil. When the implement is to undergo inoperative transport, the hydraulic system of the tractor or other towing vehicle is operated to extend the piston rods of the assemblies 65 fully from their cylinders to that substantially the position that is shown in FIG. 12 of the drawings is achieved in which the free end or tips of the blades 44, 46 or 47 of the tines 8 are spaced above the ground surface by a distance which is at least equal to substantially the radius of one of the ground wheels 62.

FIGS. 13 to 14 of the drawings illustrate a further alternative implement or machine in accordance with the invention, said implement having only a single main frame beam 74 that extends substantially horizontally transverse, and usually substantially horizontally perpendicular, to the intended direction of operative travel A. The single main frame beam 74 is, however, similar in formation and disposition to one of the previously described frame beams 1 and 2. Six support plates 75 are secured to the frame beam 74 at regular intervals along the length thereof and it will be seen from FIG. 14 of the drawings that each support plate 75 projects above the frame beam 74 and rearwardly thereof with respect to the direction A, the two end support plates of the row of six thereof being spaced from the adjacent ends of the frame beam 74 by distances which are substantially half the distance by which neighbouring plates 75 in the row are spaced apart from one another. As in the preceding embodiments, each support plate 75 has a corresponding one of the tines 8 connected to it by one of the pivotable quadrilateral linkages 18, the latter comprising the pivot bearings which include the stub shafts 4, 6, 9 and 11. The tines 8 are moved, during the operation of the implement, by a transmission that is substantially identical to the transmission which has been described above and which therefore includes six of the eccentric mechanisms 21, the composite shaft 24 and the central gear box 30. However, in this embodiment, the housings of the shaft bearings 25 are connected to the top of the frame beam 74 by brackets 76 that are inclined upwardly and forwardly with respect to the direction A from the beam 74 at a somewhat steeper inclination to the horizontal than in the case of the previously described brackets 26. The central gear box 30 is, in this embodiment, carried by a transverse support 77 that lies between the upwardly convergent limbs of a coupling member or trestle 78 that is similar in many respects to the coupling member or trestle 32 that has been described above. In this connection, it will be noted that the top of the coupling member or trestle 78 is provided with the parts 49 to 55 inclusive that have already been described above with particular reference to FIG. 5 of the drawings. The opposite ends of the hollow main frame beam 74 are closed by substantially vertically disposed side plates 79 that are parallel to one another and substantially parallel to the direction A, said side plates 79 being similar to the side plates 35 that are illustrated in FIGS. 1 and 2 of the drawings except that the side plates 79 have a somewhat reduced extent in the direction A as compared with the side plates 35. The side plates 79 project both forwardly beyond and rearwardly behind the frame beam 74 and each of them is formed, in the projecting portions, with corresponding curved rows of holes 80. Arms 82 are arranged alongside the respective plates 79 and each of them is formed with two holes that can register with chosen ones of the holes 80 in the corresponding rows, two bolts 81 being provided for substantially horizontal disposition in the holes in each arm 82 and the corresponding chosen holes 80. The arms 82 project rearwardly by some distance behind the side plates 79 and the rearmost end of each arm 82 carries a corresponding substantially horizontal axle shaft that projects inwardly therefrom towards the center of the implement, said axle shaft having a pneumatically tired supporting ground wheel 83 mounted thereon in a freely rotatable manner. As in the case of the first embodiment, the level at which the frame of the implement will be disposed above the ground surface can be adjusted by altering the positions of the arms 82 relative to the side plates 79 employing the bolts 81 to maintain any chosen position of ajustment.

Three parallel and horizontally spaced apart supports 84 of which only two are clearly visible in the drawings are fastened to the top of the frame beam 74 so as to extend substantially parallel to the direction A and project both forwardly beyond, and rearwardly behind, the beam 74. The leading end of each support 84 with respect to the direction A is rigidly secured to the center of a corresponding transverse beam 85 that extends substantially horizontally perpendicular to the direction A and thus substantially parallel to the longitudinal axis of the main frame beam 74. The opposite ends of each transverse beam 85 lie in register, in the direction A, with a corresponding immediately neighbouring pair of the support plates 75 and said ends carry substantially vertically disposed sleeves 86 in each of which a corresponding substantially vertically disposed stub shaft 87 is turnably mounted. The lower end of each stub shaft 87 projects from beneath the bottom of the sleeve 86 concerned and is there secured to the base of a corresponding fork 88 whose limbs are inclined obliquely downwardly and rearwardly towards the ground surface therefrom (see FIG. 14). The lower and rear ends of the limbs of each fork 88 are perpendicularly interconnected by a corresponding axle pin upon which a disc coulter 89 is mounted so as to be freely rotatable between the limbs of the fork 88 concerned. Each disc coulter 89 is located a short distance in advance of the corresponding hook-shaped tine 8 with respect to the direction A and is disposed vertically above the blade 44, 46 or 47 of that tine.

The rear edges of the upwardly convergent plates of the coupling member or trestle 78 have the leading surface of a hollow substantially horizontally disposed beam 90 of square cross-section rigidly secured to them at a level that is a little above half way between the top and bottom of said member or trestle 78. The opposite ends of the beam 90 carry rearwardly extending arms 91 whose vertical widths progressively decrease from said beam 90 towards the free ends of the arms (see FIG. 14). The rear ends of two of the three supports 84 are secured to a further transverse beam 92 that extends substantially horizontally parallel to the beam 90 throughout a greater transverse width than the latter, said beam 92 being only marginally shorter in length than the main frame beam 74. Both the top and the bottom of the frame beam 92 are provided at six regularly spaced locations along its length with pairs of upwardly and downwardly projecting lugs 93, said locations being in register with the tines 8 in the direction A as seen in FIG. 13 of the drawings. The two lugs 93 of each pair support a corresponding substantially horizontal pivot pin and upper and lower pairs of arms 94 are turnable upwardly and downwardly about said pivot pins at the relatively remote sides of the two lugs 93 of each pair. The pairs of arms 94 form parts of parallelogram linkages, their rearmost ends being connected by further parallel pivot pins to upper and lower pairs of lugs 95 that are mounted on a beam 96 which extends substantially horizontally parallel to the beam 92 but which beam 96, it will be realised, is movable upwardly and downwardly relative to the beam 92 through the intermediary of the intervening parallelogram linkages. The front of the beam 96 with respect to the direction A is provided at six locations with corresponding substantially vertically disposed sleeves 97, said six locations being between the two arms 94 of each of the six pairs as seen in plan view. Each sleeve 97 receives a corresponding upwardly and downwardly adjustable outlet tube 98, the axial position thereof relative to the sleeve 97 concerned being fixable by a corresponding set bolt 107. Each outlet tube 98 terminates, at a level beneath that of the beam 96, in a downward and rearwardly curved sowing shoe 99 while its upper end communicates by way of a telescopic sleeve 100 with a corresponding outlet 101 at the bottom of a hopper 102 that forms part of a seed drill 102A. The hopper 102 extends substantially horizontally parallel to the main frame beam 74 throughout substantially the whole of the effective working width of the implement (see FIG. 13).

Supports 103 in the form of downwardly and forwardly inclined pairs of arms are connected to the bottom of the beam 96 in register with each of the outlet tubes 98 and sowing shoes 99, the leading lower end of each support 103 rotatably carrying a corresponding ground engaging wheel or roller 105. Further supports 104 that are of similar formation to the supports 103 project downwardly and rearwardly with respect to the direction A from the rear surface of the beam 96 at locations which also register in the direction A with the outlet tubes 98 and sowing shoes 99, the lower rearmost end of each further support 104 rotatably carrying a corresponding ground engaging wheel or roller 106. The hopper 102 of the seed drill 102A is of course, supported by the rearmost ends of the two arms 91 and it will be seen from FIGS. 13 and 14 of the drawings that, nearer their leading ends, said arms 91 also carry a cylindrical tank or hopper 108 that forms part of a mechanism 109 for inserting a liquid, or at least fluid, chemical substance into the soil. The drawings show the tank or hopper 108 of the mechanism 109 in the form of a tank that may contain, for example, liquefied ammonia and, in such a case, the tank 108 is of such a construction as to enable the liquefied ammonia to be contained safely and reliably therein. It comprises a pressure-resistant filling opening and a plurality of outlets 110 each of which has its own pressure-resistant shut-off valve. Each outlet 110 is connected, downstream of the corresponding shut-off valve, to one end of a flexible hose 111 whose opposite end, in turn, is connected to the upper end of a substantially vertically disposed tubular injector 112 whose lowermost end penetrates downwardly into an upper layer of the top soil when the implement is in operation at a location in register with one of the tines 8 considered in the direction A. There are six of the injectors 112 in the embodiment that is being described and each of them is connected to the transverse beam 92 by way of a substantially vertical sleeve provided with a set bolt so that each injector 112 can be adjusted upwardly or downwardly in position relative to the transverse beam 92.

In the use of the soil cultivating implement or machine that has been described with reference to FIGS. 13 and 14 of the drawings, its tines 8 are caused to move upwardly and downwardly in a repetitive vibratory manner in the same way as has already been described with reference to the preceding embodiments. However, in this case, a somewhat more uniform break up of the soil is achieved because the soil is already cut loose in front of, and above, the tines 8 by the disc coulters 89, the uniformly well broken condition of the soil that is achieved by the disc coulters 89 and tines 8 being beneficial to the efficient operation of the injectors 112 of the following mechanism 109 and/or the sowing shoes 99 of the seed drill 102A. The implement or machine of FIGS. 13 and 14 of the drawings can, for example, be used in cultivating, fertilising and seeding an uncultivated field. The upwardly and downwardly vibrating tines 8 follow the disc coulters 89 and six laterally spaced apart furrows are formed into which, immediately behind the tines 8, seed, fertilisers growth stimulating and/or other chemical substances are inserted by the injectors 112 of the mechanism 109. The six leading ground engaging wheels or rollers 105 immediately follow th the injectors 112 in the direction A and wholly or partially close the furrows to ensure a high degree of retention of the chemical substance or substances that has or have been introduced by the mechanism 109. The furrows are reopened by the six seed shoes 99 which insert seeds into the soil in corresponding rows, the furrows being closed again, behind the shoes 99, by the ground engaging wheels or rollers 106 so that the seeds have a satisfactory environment in which to germinate. Thus, in a single operation, a field can be cultivated, fertilised and seeded without the necessity for any pretreatment.

Although various features of the soil cultivating implements or machines that have been described and/or that are illustrated in the accompanying drawings will be set forth in the following claims as inventive features, it is emphasised that the invention is not necessarily limited to those features and that it includes within its scope each of the parts of each soil cultivating implement or machine embodiment that has been described, and/or that is illustrated in the accompanying drawings, both individually and in various combinations.

What I claim is:

1. A soil cultivating implement comprising a frame and a plurality of soil working members being pivotably connected to said frame by corresponding polygonal linkages, driving means connected to rock said linkages and pivot said members up and down about substantially horizontal axes during operation, said members comprising fastening portions and forwardly extending soil working portions that are vertically displaced during operation to loosen soil, the amplitude of repetitive vertical displacement of points along the lengths of said soil working portions being greater rearwardly from their leading ends, at least one polygonal linkage having vertically spaced apart pivotal axes that extend substantially horizontally transverse to the direction of travel and said pivotal axes being located at different levels and behind one another, said linkage having two forward pivots interconnected to the frame and two trailing pivots interconnected to the fastening portion of said member, the distance between the two forward pivots being less than the distance between the two trailing pivots when viewed from the side.

2. An implement as claimed in claim 1, wherein a drive transmission to the linkage of each of said soil working members comprises a respective eccentric mechanism.

3. An implement as claimed in claim 2, wherein said linkage includes at least one upper arm link and at least one lower link, said transmission including an eccentric with a projecting arm connected to the upper link between the two upper pivots.

4. An implement as claimed in claim 3, wherein each projecting arm extends substantially horizontally and is connected to a ring of the corresponding eccentric mechanism, said ring rotatably surrounding an eccentrically mounted disc, the discs that correspond to the eccentric mechanisms being mounted on a common driving shaft.

5. An implement as claimed in claim 4, wherein each eccentric disc is arranged on a separate portion of said shaft and the separate portions of the common driving shaft being releasably interconnected by sleeves, the separate portions of said shaft located adjacent the center of the implement being releasably connected to an output shaft of a gear box, said output shaft being in driven connection with an input shaft via bevel pinions housed within said gear box, said input shaft extending forwardly and being connectable to the power take-off shaft of a tractor.

6. An implement as claimed in claim 1, wherein a straight line between the upper two pivots intersects a further straight line between the lower two pivots, the point of intersection being located directly above the leading end of said soil working member in the latter's lowermost position.

7. An implement as claimed in claim 6, wherein the two straight lines substantially coincide, as seen in side elevation, with the longitudinal axes of upper and lower links of each polygonal linkage.

8. An implement as claimed in claim 7, wherein at least one soil working member comprises a substantially planar tine having a hook-shaped configuration as seen in side elevation, said tine having a leading end in advance of the connections of the fastening portion of said tine to links of the corresponding linkage, each tine including a downwardly and forwardly inclined substantially straight portion that terminates in a forwardly directed portion, the end of the latter portion being located substantially directly beneath the point of the intersection of said lines when viewed in side elevation with said tine at substantially the lowermost end of its path of repetitive motion.

9. An implement as claimed in claim 8, wherein said forwardly directed portion has a lower substantially horizontal edge and the upper edge of said portion is inclined upwardly and rearwardly with respect to the direction of travel, away from the leading part, a substantially planar element being mounted on said upper edge.

10. An implement as claimed in claim 9, wherein said element has a substantially isosceles triangular configuration and the base thereof forms at the rear of the element.

11. An implement as claimed in claim 6, wherein the distance between the two upper pivots of said linkage is substantially the same as the distance between the two lower pivots, the distance between the two forward pivots being substantially four-fifths the distance between the two rear pivots.

12. An implement as claimed in claim 1, wherein said pivotal axes are defined by stub shafts mounted in bearing sleeves and maintained in position by blocking plates.

13. An implement as claimed in claim 1, wherein said frame is supported on at least one ground wheel and means adjusting said wheel upwardly and downwardly relative to said frame, said wheel being pivoted to said frame and movable to either one of two different positions relative to the frame, said wheel being located in advance of the soil working members with respect to the direction of travel in one of said positions and to the rear of the frame in the second position.

14. An implement as claimed in claim 13, wherein there are two ground wheels adjacent opposite ends of a row of said soil working members, the two ground wheels being mounted on arms and said arms being displaceable to either one of said two positions, said arms projecting forwardly from the frame in said one position and rearwardly from the frame in the second position.

15. A soil cultivating implement comprising a frame and a plurality of soil working members being pivotably connected to said frame by corresponding quadrilateral linkages, driving means connected to rock said linkages and pivot said members up and down about substantially horizontal axes, said members comprising upper fastening portions and lower soil working portions that extend forwardly to leading ends, said soil working portions being driven through repetitive vertical movements and the amplitude of vertical displacement of points along the lengths of the soil working portions being greater rearwardly from their leading ends, at least one of said linkages having four vertically spaced apart pivotal axes that extend substantially horizontally transverse to the direction of travel and said pivotal axes being located at different levels, behind one another, said linkage having upper and lower links and the forward ends of the links being pivoted to the frame, the trailing ends of the links being pivoted to the fastening portions, the distance between the pivotal axes that connect the links to the frame being less than the distance between the two pivotal axes that connect the links to said fastening portions, whereby the leading ends remain at substantially constant depths below the ground, means supporting the frame and soil working portions at any one of a plurality of different levels during operation.

16. An implement as claimed in claim 15, wherein at least one mechanism for inserting material into the soil during operative progress of the implement is connected to the frame at the rear of said members.

17. An implement as claimed in claim 16, wherein there are two mechanisms that dispense materials into the soil one behind the other with respect to the normal direction of implement travel, a first mechanism being positioned to insert chemical substances into the soil and a second mechanism being positioned to sow seeds.

18. An implement as claimed in claim 17, wherein the first mechanism is located immediately to the rear of the soil working members and comprises a plurality of injectors that are in register, with respect to the direction of travel, with corresponding soil working members, said second mechanism being linked to said frame and comprising a plurality of outlets that are in communication with corresponding sowing shoes, said sowing shoes being in register with corresponding soil working members.

19. An implement as claimed in claim 15, wherein a three-point coupling trestle is secured to the front of said frame and said trestle comprises resilient connection means that interconnects said implement to a tractor and reduces shocks caused during operation.

20. An implement as claimed in claim 19, wherein said trestle comprises an upper coupling point that is flexibly interconnected to said frame through blocks of resilient material, said resilient material being located inside an elongated housing and a rod extending through said material, the opposite ends of the housing being open and said rod extending lengthwise through the housing to a coupling at its leading end.

21. An implement as claimed in claim 20, wherein said housing is polygonal in cross-section.

22. An implement as claimed in claim 15, wherein ground wheels are pivoted to the lateral sides of the frame by a foldable linkage, said wheels being bodily displaceable relative to the frame by at least one fluid pressure operated piston and cylinder assembly that links pivoted parts of the foldable linkage to one another, said wheels being displaceable to ground engaging locations which correspond to an inoperative transport position of the implement in which the soil working members are raised above the ground surface.

* * * * *